United States Patent
Gundersen

(10) Patent No.: US 8,689,387 B2
(45) Date of Patent: Apr. 8, 2014

(54) PAD WITH BRUSH/SCRUB FUNCTION

(75) Inventor: Dag H Gundersen, Tolvsrød (NO)

(73) Assignee: Pad Tech AS, Oslo (NO)

( * ) Notice: Subject to any disclaimer, the term of this patent is extended or adjusted under 35 U.S.C. 154(b) by 505 days.

(21) Appl. No.: 13/056,983

(22) PCT Filed: Aug. 11, 2009

(86) PCT No.: PCT/NO2009/000282
§ 371 (c)(1),
(2), (4) Date: May 2, 2011

(87) PCT Pub. No.: WO2010/019048
PCT Pub. Date: Feb. 18, 2010

(65) Prior Publication Data
US 2011/0232565 A1    Sep. 29, 2011

Related U.S. Application Data

(60) Provisional application No. 61/103,941, filed on Oct. 9, 2008.

(30) Foreign Application Priority Data

Aug. 13, 2008  (NO) .................................. 20083511

(51) Int. Cl.
A47L 13/16    (2006.01)
A47L 13/19    (2006.01)
A47K 7/00     (2006.01)

(52) U.S. Cl.
USPC ........... 15/104.94; 15/209.1; 15/223; 15/227; 401/7

(58) Field of Classification Search
USPC ........ 15/104.93, 208, 209.1, 210.1, 223, 224, 15/226, 227; 401/7
See application file for complete search history.

(56) References Cited

U.S. PATENT DOCUMENTS 3,495,918 A * 2/1970 Leland .......................... 401/201
4,674,237 A     6/1987 Sullivan
6,811,338 B1 * 11/2004 Manske et al. .................... 401/7

(Continued)

FOREIGN PATENT DOCUMENTS

DE    3441594 A      5/1986
EP    0078596-X      5/1983

(Continued)

OTHER PUBLICATIONS

Office action of JP patent Office dated Oct. 10, 2013 (with translation), submitted inter alia as a statment of relevance for non-English references cited therein.

*Primary Examiner* — Mark Spisich
(74) *Attorney, Agent, or Firm* — Christian D. Abel

(57) ABSTRACT

The present application relates to a laminated pad (1) that is used to apply a liquid or a colloidal substance in a controlled manner onto a surface. The laminated pad comprises at least one storage layer (4), where the storage layer when provided with through-going cuts (8) and welded to an impermeable pocket layer (5) due to its resilient characteristics, will form an upwardly standing surface in the cutting area. The upwardly standing surface will act as a brush and/or scrub or a transfer device, whereby the brush or scrub can be used to treat the surface to which a substance is to be applied, before or during the appliance of the substance.

11 Claims, 2 Drawing Sheets

(56) References Cited

U.S. PATENT DOCUMENTS

Figure 1:
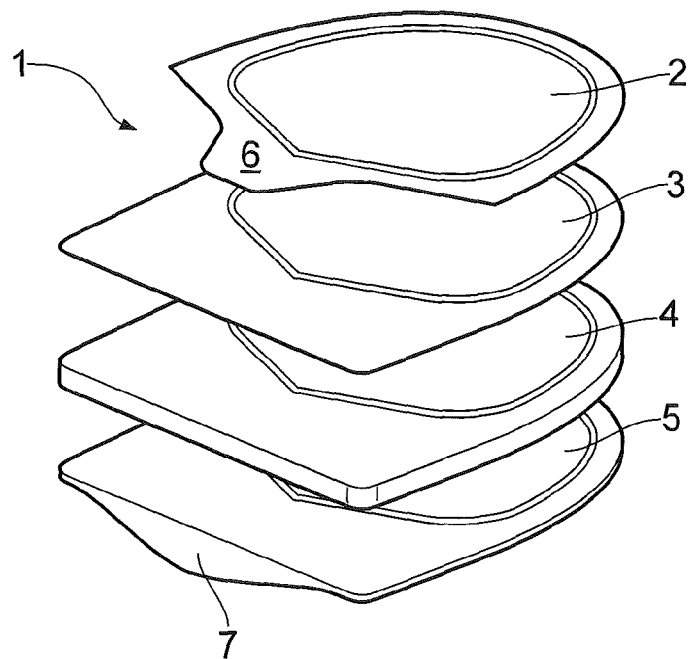

| | | |
|---|---|---|
| 2002/0118993 A1 | 8/2002 | Lafosse-Marin et al. |
| 2005/0075255 A1 | 4/2005 | McAtee |
| 2007/0048062 A1 | 3/2007 | Brunner |
| 2007/0157410 A1 * | 7/2007 | Yamada ................. 15/229.4 |

FOREIGN PATENT DOCUMENTS

| | | |
|---|---|---|
| EP | 0945251 A | 9/1999 |
| GB | 2130965 A | 6/1984 |
| JP | 06-014859 | 1/1994 |
| JP | 2002-519080 | 1/2000 |
| JP | 2001-269222 | 10/2001 |
| JP | 2002-262931 | 9/2002 |
| NO | 20074383 E | 3/2009 |
| WO | 00/00056 | 1/2000 |
| WO | WO01/92622 A | 12/2001 |
| WO | WO2008/065551-X | 6/2008 |
| WO | WO2009/028952 A | 3/2009 |

* cited by examiner

PAD WITH BRUSH/SCRUB FUNCTION

This application is a national stage of PCT/NO09/00282, filed 11 Aug. 2009, and claims priority of U.S. Provisional Application No. 61/103,941, filed 9 Oct. 2008.

The present invention relates to a device for delivering and applying of one or more doses of a fluid or colloidal substance at a desired surface, such as a liquid, creamy, gelatinous, gaseous or powdery substance, as well as to a device for treatment of surface of the desired surface. The device of the present invention applies especially to the delivery of a pharmaceutical, cosmetic, hygienic, perfumery and household-cleaning substances.

In a number of different applications there is a need for a device that is adapted to applying a substance on a desired surface or spot. This may involve, for example, the application of shoe cream, cosmetics, moisture creams, cleansing creams, self-tanning creams, various gel products for personal hygiene, or for example soap, detergent or similar substances. Various liquids such as, for example, nail varnish, varnish remnants, glue remnants or the like also have to be applied in the right amount at the right place under controlled conditions.

The substance that is to be applied can be stored for instance in a bottle, where the user pours a suitable amount of the substance on his/hers hands and then manually spreads the substance on the desired surface. One other method is to have separate bottles and applicator elements. The substance is then applied onto the applicator element, which will soak up a quantity of the substance, whereby the user will use the applicator element to disperse the substance on a desired surface or spot.

Yet another method to apply a substance on a desired surface is to use a disposable or single-use applicator that is supplied with a pre-determined quantity of a substance. Such applicators are manufactured from a disposable material substantially fully infused with the appropriate substance and sealed in a container.

Common for all known devices is that they will result in that the user will soil his or hers hands, either by bringing the substance in direct contact with their hands, or by that the device will leak and/or desiccate. Furthermore, none of the known devices are able to treat the surface or spot that is to be applied a substance.

Norwegian patent application NO 2007 4383 describes a device for applying a product in a more controlled manner onto a surface. The device comprises several layers, where the layers accommodate a storage receptacle or a storage layer containing the product to be applied. The product contained in the device is transported to the surface of application, through a two-pieced top layer, where one piece of the top layer acts like a valve layer while the other piece acts like an applicator and distribution layer.

It is therefore an object of the present invention to provide a disposable laminated pad for containing and dispensing a liquid or colloidal substance in a convenient, uniform and simple manner to a desired surface.

It is also an object of the present invention to provide a disposable laminated pad which also treats the desired surface before or during the application of the liquid or colloidal substance on the surface.

It is a further object of the present invention to provide a disposable pad that can store the liquid or colloidal substance over long periods without the pad deteriorating.

These objectives are achieved with a disposable laminated pad for treating and applying a liquid or colloidal substance onto a surface according to the invention as defined in the enclosed independent claim, where embodiments of the invention are given in independent claims.

The present invention regards a laminated pad, where the laminated pad can be used to treat a desired surface before or during the applying of a liquid or colloidal substance onto the surface. The laminated pad comprises several material layers that are connected to each other in an appropriate way. Each of the layers in the laminated pad has its own specific function. A specific function for the laminated pad may also be obtained by combining two or more of the layers.

The laminated pad according to the present invention is primarily intended to be utilized as an applicator for the human body, but it may also be used in the household.

A typical laminated pad that contains a liquid substance may, for instance, consist of four layers, where a storage layer and a contact layer are arranged between a top layer and a pocket layer. The top layer and the pocket layer in this case are manufactured from a material that is substantially liquid impermeable, whereby this will involve the storage layer and the contact layer being enclosed between the two outer layers, i.e. between the top layer and the pocket layer. By joining or bonding the different layers together, the laminated pad will form a sealed compartment, which will not leak when the laminated pad is transported, stored or used.

In order to simplify the use of the laminated pad, a side of the pocket layer that is facing away from the other layers may be provided with a holding device. The holding device is in its simplest form a cover that is attached to the pocket layer in order to form an open cavity, into which cavity a hand, finger or a utensil may be put into when the laminated pad is used. The cover may be manufactured from an elastic non-woven material.

However, if the content in the laminated pad is a more viscous substance, or if one or more of the layers are pre-impregnated with a dry substance, it will not be necessary to use a top layer.

The top layer may also be used, even if it is not necessary to provide a sealed construction. The purpose of the top layer in these cases will then be to protect the underlying layer or layers from dirt and/or outer exposure, whereby the layer may be manufactured from a cheaper material.

The degree of "sealing" will therefore be dependent on the substance that is to be stored within the laminated pad.

Depending on the properties of the liquid or colloidal substance to be stored, the laminated pad can be filled with an appropriate amount of the substance either before the joining of the different layers, or after the layers have been joined together. In this case the substance has to be supplied through one or more of the layers, for instance by a needle.

In some applications it is not necessary to seal the laminated pad by using the top layer, as the substance that is stored in the storage layer is such it will not leak, evaporate etc.

When using the top layer, the top layer is joined to the underlying layers for example by welding. As the top layer has to be removed before the laminated pad is used, the top layer is welded in an area along its outer periphery, where the weld strength is adjusted to ease the removal of the top layer. The welding of the different layers may also be accomplished in order to form separate compartments in the laminated pad, where this for instance may be desirable if the laminated pad contains two or more substances which are not to be in contact with each other before the pad is used. The welding will then separate the different substances, whereby the removal of the top layer will allow the different substances to be mixed and/or to react with each other.

In order to create a brush or scrub function, one or more of the layers are provided with cuts along their surfaces, where the cuts can be through-going or partly through-going the layer material. After the cuts are made, the layer or layers are welded to the pocket layer. As the material from which the different layers are manufactured has a certain (resilient) property, the bonding with the pocket layer will result in that the material layer(s) being compressed ("stretched") along the welding seam. This will cause the cut edge(s), due to the compression or stretching of the layer(s), to rise upwardly from the surface of the layer.

The different layers may be cut or perforated in the same pattern, where the layers in this case are placed on top of each other and then cut together in the same operation. The layers may also be provided with different cutting patterns. In this case each layer is cut individually, whereby the layers are put together before they are welded. The layers are then arranged in such a way that the cutting lines will form an angle with each other.

The cutting may be performed as continuous lines, discontinuous lines, curved lines or even as perforations. Furthermore, it is also possible to vary the thickness and/or length of the cuts.

It should be understood that the laminated pad according to the present invention may consist of one or several different layers, depending on the specific use of the laminated pad.

The different layers of the laminated pad may be manufactured from different materials, where the materials furthermore may have different thickness, different properties etc. The layers may also differ in size, form and the way in which they are positioned in proportion to each other.

The welding of the different layers may be carried out by ultrasound, laser, heat welding etc. Furthermore, the welding may be a string or line, or it may be a spot weld.

The cutting may be carried out by knife, laser, ultrasound etc.

Figure 2:
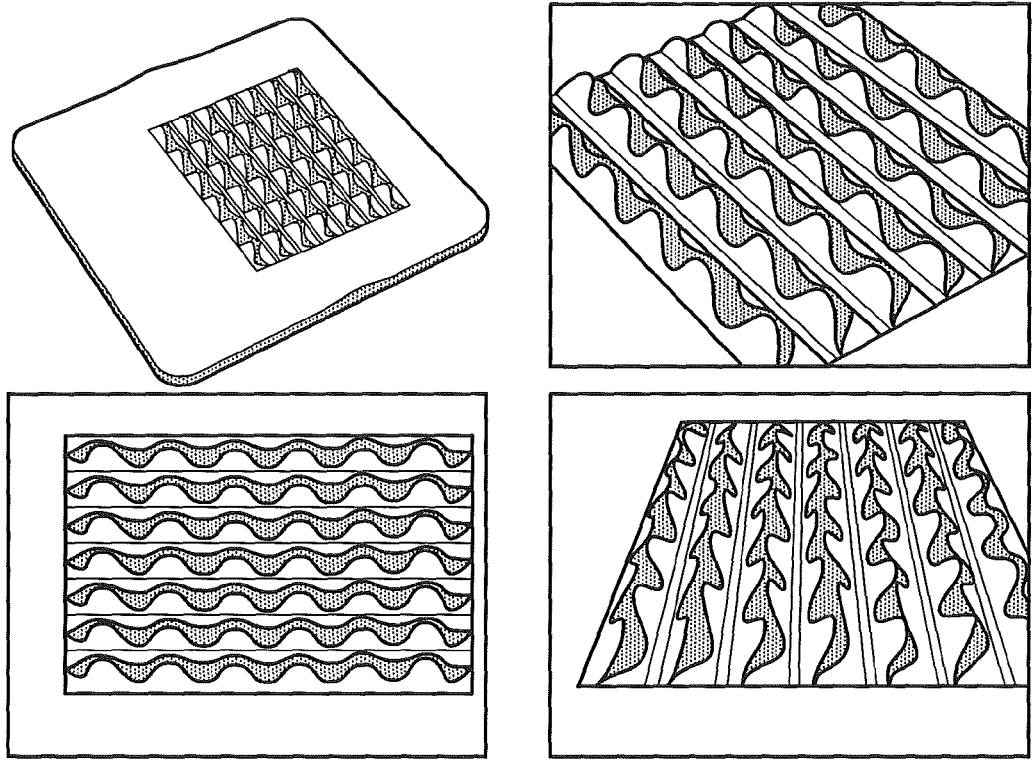
Figure 3:
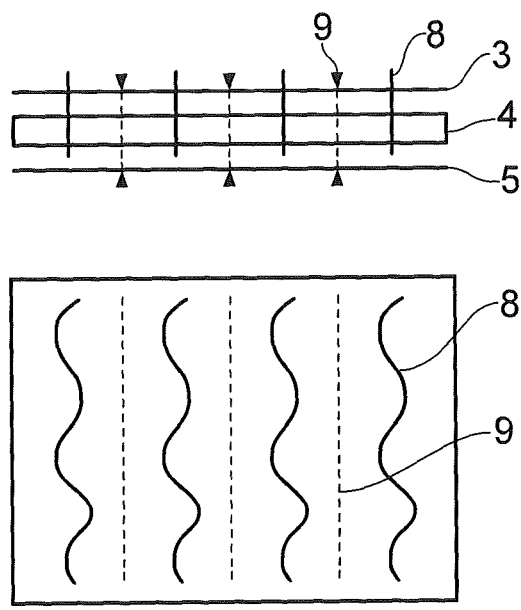
Figure 4:
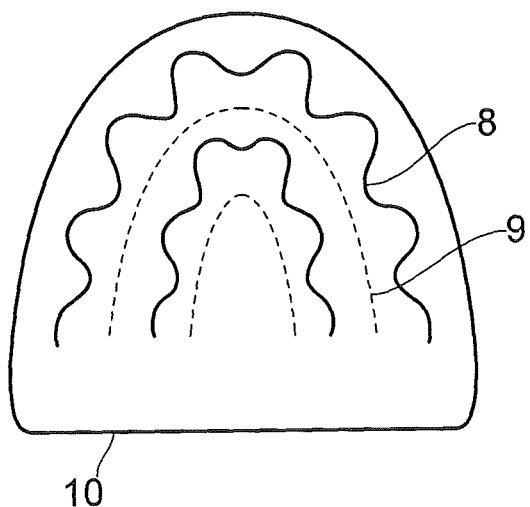

Having thus generally described the nature of the present invention, reference will now be made to the accompanying drawings, showing by way of illustration the preferred embodiments thereof, in which:

FIG. 1 is an exploded view showing the principal configuration of a device according to the present invention, FIG. 2 shows the build-up of a brush or scrub function according to the present invention, FIG. 3 shows the cutting and welding connections between various layers of the device according to the present invention, where the device is shown in a cross section and from above, and FIG. 4 shows a finished pad according to the present invention.

FIG. 1 shows an embodiment of a disposable hand-held laminated pad according to the present invention, where the laminated pad 1 comprises four different layers 2-5. Each layer has its own function, but one can also obtain a specific function by combining two or more of the individual layers 2-5.

If the laminated pad 1 is to contain a liquid or a corresponding substance that may leak, the laminated pad 1 is sealed up with a top layer 2 which acts as a protective cover. The top layer 2 is to be removed by tearing before the laminated pad 1 is used, and the top layer 2 is therefore attached in an area along its periphery to the remaining layers 3-5 of the pad. This attachment can be done in many different ways, for instance welding by ultrasound, heat welding, gluing etc. In order to ease the removing of the top layer 2, the top layer 2 is formed with a flap or corner 6.

The top layer 2 is manufactured from a substantially impermeable material.

A pocket layer 5 forms the other outer side of the laminated pad 1, this meaning that the other layers 2-4 are arranged within the top layer 2 and the pocket layer 5. As the pocket layer 5, like the top layer 2, must prevent the liquid or colloidal substance passing through it during the transport, storage or use of the laminated pad 1, the pocket layer 5 is made from a liquid-impermeable material.

The pocket layer 5 is attached to the overlaying layers 2-4 by way of welding, gluing or the like.

The pocket layer 5 is on its side that is turning away from the storage layer 4 provided with a holding device 7. The holding device 7 is a cover that is attached to the pocket layer 5 in order to form an open cavity, into which cavity a hand, finger or utensil may be put when the laminated pad 1 is used. The cover 7 is manufactured e.g. from an elastic and/or non-woven material.

This configuration will give that the top layer 2 and the pocket layer 5 will encircle or include the contact layer 3 and the storage layer 4 in the shown embodiment. This will provide a laminated pad 1 that can be transported and/or stored without being accidentally opened, desiccated or deteriorated. Furthermore, the user will not be in contact with the liquid or colloidal substance that the laminated pad 1 contains during the use of the laminated pad 1. This is particularly advantageous if the substance is irritating for the skin.

The storage layer 4 is arranged above the pocket layer 5. As the storage layer 4 contains the liquid or colloidal substance that is to be applied onto a surface, the storage layer has a certain thickness. It is manufactured from a non-woven material, for instance a fiber structure, where the material has sufficient porosity to store the substance to be applied. Depending on the nature of the substance to be stored within the storage layer 4, the substance can either be supplied to the storage layer before the different layers 2-5 are connected or bonded together, or it can be supplied after the different layers 2-5 have been connected or bonded together.

The contact layer 3 serves the function of a "passage" layer, as this layer 3 will allow the substance to pass through from the storage layer 4 and to the surface on which the substance is to be applied. The contact layer 3 is manufactured from for example a non-woven material or a perforated plastic material.

Sometimes it is necessary to treat the surface that is to be applied with the substance contained in the laminated pad 1. According to the present invention, the pocket layer 5, storage layer 4 and the contact layer 3 are manufactured in such a way that they together provide a brush and/or scrub unit. This brush and/or scrub will then clean or remove dirt from the desired surface, whereafter the liquid or colloidal substance is applied onto the surface.

The brush and/or scrub will also act as a transfer device; if the laminated pad 1 contains, for instance, a dry deodorant powder, the brush and/or scrub will due to the back and forth motion in the armpit "throw" the deodorant powder from the laminated pad 1 and over to the armpit.

Referring now to FIG. 2, the structure of the brush and/or scrub unit is shown. As mentioned above, the brush and/or scrub unit in this embodiment is comprised of the pocket layer 5, the storage layer 4 and the contact layer 3. Each of the layers 3-5 is manufactured from a material that has a certain tensile strength. When the contact layer 3 and the storage layer 4 are cut in identical or different patterns 8, and thereafter connected together with the pocket layer by welding 9, the tensile strength and the compression of the material in the layers 3-4 will tend to lift the material in the cut area. This will provide upstanding surfaces on the side of the contact layer 3 that is facing the surface that is to be treated and applied a substance.

FIG. 3 shows very schematically how the brush and/or scrub unit is constructed. First the contact layer 3 and the storage layer 4 are cut in a desired pattern 8, where this pattern 8 will depend on the characteristics of the substance to be stored. The contact layer 3 and the storage layer 4 in this embodiment are cut in the same pattern 8 as the layers 3, 4 are placed on top of each other whereby the cutting is performed. Is should be understood that this cutting can also be performed for each layer 3, 4 independently, for instance if the two layers 3, 4 are supposed to have different cutting patterns.

The cutting can be done with a knife, ultrasound, laser etc.

The cutting pattern in the shown embodiment is waved and continuous for both layers 3, 4, but it may have any form. The cutting line may further be discontinuous, partly cut through the layer(s) 3, 4 etc.

When the contact layer 3 and the storage layer 4 are cut ready, the three layers 3, 4, 5 are arranged overlaying each other, whereby they are welded 9 together. This welding 9 is done by ultrasound, heat welding, laser etc. The welding will entail that the layer material in each layer will be stretched along the welding lines, where this stretching will "pull" the material towards the welding lines 9 thus lifting up the cutting edges. In the shown embodiment the cutting is done in a waveform, which will give the brush and/or scrub unit a corrugated or waved surface.

A laminated pad 1 according to the present invention is shown in FIG. 4, where the laminated pad 1 is formed as a glove or mitt, in which the user can insert his or her hand, finger, utensil etc. The cutting pattern 8 is waved and arranged a certain distance inside the periphery of the laminated pad 1. The straight end 10 forms the opening for the users hand and is therefore not cut or welded.

Further modifications and alternative embodiments of the present invention will be apparent to those skilled in the art in view of this description. Accordingly, this description is to be construed as illustrative only and is for purpose of teaching those skilled in the art the manner of carrying out the invention. It is to be understood that the forms of the invention shown and described herewith, are to be taken as the presently preferred embodiment. Various changes may be made in the shape, size and arrangement of parts.

The invention claimed is:

1. A laminated pad for applying a liquid or a colloidal substance in a controlled manner onto a surface, where the laminated pad comprises at least one layer that is connected in an area around its periphery to a pocket layer, the layer containing the liquid or colloidal substance to be applied, wherein the at least one layer is manufactured from a material having a tensile strength, the layer being cut along it surface to provide at least one through-going cut in the surface, the layer being welded to the pocket layer such that the welding stretches the layer along the welding lines, thereby providing an upstanding surface in the area of the at least one through-going cut where the upstanding surface will provide the laminated pad with a brush and/or scrub function.

2. A laminated pad according to claim 1, wherein the pocket layer is manufactured from a substantially impermeable material.

3. A laminated pad according to claim 1, wherein the laminated pad further comprises a substantially impermeable top layer.

4. A laminated pad according to claim 1, wherein the at least one through-going cut is arranged in different patterns on a part of or the whole surface of the at least one layer.

5. A laminated pad according to claim 1, wherein the layer consists of fiber structures in one or more planes, the fiber structures forming cavities containing the substance.

6. A laminated pad according to claim 1, wherein a holding device is attached to an outside of the pocket layer.

7. A laminated pad according to claim 1, wherein the laminated pad comprises additional layers, where the layers are provided with at least one through-going cut, and the layers further being welded to each other.

8. A laminated pad according to claim 1, wherein the at least one through-going cut along the surface of the layer is a perforation.

9. A laminated pad according to claim 1, wherein layer is provided with different cutting patterns.

10. A laminated pad according to claim 1, wherein the layers have different forms.

11. A laminated pad according to claim 1, wherein the layers are manufactured from a material that has resilient characteristics.

* * * * *